United States Patent
Ojiro et al.

(10) Patent No.: US 11,304,613 B2
(45) Date of Patent: *Apr. 19, 2022

(54) BAG-SHAPED STRUCTURE, CUFF, AND BLOOD PRESSURE MONITOR

(71) Applicants: OMRON CORPORATION, Kyoto (JP); OMRON HEALTHCARE CO., LTD., Muko (JP)

(72) Inventors: Shuhei Ojiro, Kyoto (JP); Kazuyoshi Nishikawa, Ritto (JP)

(73) Assignees: OMRON CORPORATION, Kyoto (JP); OMRON HEALTHCARE CO., LTD., Muko (JP)

( * ) Notice: Subject to any disclaimer, the term of this patent is extended or adjusted under 35 U.S.C. 154(b) by 284 days.

This patent is subject to a terminal disclaimer.

(21) Appl. No.: 16/349,083

(22) PCT Filed: Dec. 26, 2017

(86) PCT No.: PCT/JP2017/046647
§ 371 (c)(1),
(2) Date: May 10, 2019

(87) PCT Pub. No.: WO2018/124074
PCT Pub. Date: Jul. 5, 2018

(65) Prior Publication Data
US 2019/0274559 A1 Sep. 12, 2019

(30) Foreign Application Priority Data
Dec. 27, 2016 (JP) .............................. JP2016-254282

(51) Int. Cl.
*A61B 5/02* (2006.01)
*A61B 5/022* (2006.01)
*A61B 5/00* (2006.01)

(52) U.S. Cl.
CPC .......... *A61B 5/02233* (2013.01); *A61B 5/022* (2013.01); *A61B 5/02208* (2013.01); *A61B 5/681* (2013.01)

(58) Field of Classification Search
CPC . A61B 5/02233; A61B 5/022; A61B 5/02208; A61B 5/681
See application file for complete search history.

(56) References Cited

U.S. PATENT DOCUMENTS 7,131,218 B2   11/2006   Schindler
7,250,030 B2   7/2007    Sano et al.
(Continued)

FOREIGN PATENT DOCUMENTS

CN   1785116 A      6/2006
CN   100382746 C    4/2008
(Continued)

OTHER PUBLICATIONS

English-language machine translation of JP-2004073230-A (Year: 2021).*

(Continued)

*Primary Examiner* — Andrey Shostak
(74) *Attorney, Agent, or Firm* — Harness, Dickey & Pierce, P.L.C.

(57) ABSTRACT

A bag-shaped structure excellent in both creep resistance and flexibility is provided. Provided is a bag-shaped structure (122) including a layer (122a) made of a thermoplastic elastomer foam. Also provided are a cuff for a blood pressure monitor and a blood pressure monitor each including the bag-shaped structure (122).

4 Claims, 6 Drawing Sheets

(56) References Cited

U.S. PATENT DOCUMENTS

| | | | |
|---|---|---|---|
| 7,794,405 B2 | 9/2010 | Karo et al. | |
| 2002/0193459 A1* | 12/2002 | Haseyama | B29C 44/348 |
| | | | 521/155 |
| 2005/0183287 A1 | 8/2005 | Schindler | |
| 2006/0129049 A1* | 6/2006 | Sano | A61B 5/02233 |
| | | | 600/499 |
| 2006/0135873 A1 | 6/2006 | Karo et al. | |
| 2009/0234381 A1 | 9/2009 | Karo | |
| 2010/0137725 A1 | 6/2010 | Takahashi et al. | |
| 2015/0081017 A1 | 3/2015 | Abbate et al. | |
| 2016/0129049 A1 | 5/2016 | Tseng et al. | |
| 2016/0354222 A1* | 12/2016 | Alsolami | A61F 5/012 |
| 2018/0355219 A1* | 12/2018 | Nagai | B29C 48/0012 |
| 2019/0261871 A1 | 8/2019 | Nishikawa et al. | |

FOREIGN PATENT DOCUMENTS

| | | | | |
|---|---|---|---|---|
| CN | 101346100 A | | 1/2009 | |
| CN | 101522097 A | | 9/2009 | |
| CN | 103665421 A | | 3/2014 | |
| JP | H09117419 A | | 5/1997 | |
| JP | 2002224056 A | * | 8/2002 | |
| JP | 2004073230 A | * | 3/2004 | |
| JP | 2006158876 A | | 6/2006 | |
| JP | 2006174860 A | | 7/2006 | |
| JP | 2007054341 A | * | 3/2007 | ............. A61B 5/022 |
| JP | 2007054341 A | | 3/2007 | |
| JP | 2007522908 A | | 8/2007 | |
| WO | WO-2008044491 A1 | | 4/2008 | |
| WO | WO-2017030141 A1 | | 2/2017 | |

OTHER PUBLICATIONS

English-language machine translation of JP-2002224056-A (Year: 2021).*
English-language machine translation of JP-2007054341-A (Year: 2022).*
International Preliminary Report on Patentability for International Application No. PCT/JP2017/046647, dated Jul. 11, 2019, (7 pages).
International Search Report and Written Opinion (in English and Japanese) issued in PCT/JP2017/046647, dated Mar. 27, 2018; ISA/JP.
Japanese Office Action dated Sep. 29, 2020 (with English translation) (10 pages).
Zhu Yunan, et al. & China Light Industry Press Ltd., "Application and modification of polypropylene plastic" dated Jan. 31, 1982 (6 pages).
Chinese First Examination Opinion Notice (with English translation) for Application No. 2017800684436 dated Apr. 6, 2021 (17 pages).
Japanese Office Action dated Mar. 30, 2021 for Japanese Patent Application No. 2016-254282 (with English translation) (9 pages).
Japanese Office Action for Japanese Patent Application No. 2016-254282 dated Aug. 24, 2021 (with English translation) (8 pages).
Chinese Office Action dated Oct. 9, 2021 for Application No. 201780068443.6 (with English translation) (16 pages).

* cited by examiner

BAG-SHAPED STRUCTURE, CUFF, AND BLOOD PRESSURE MONITOR

CROSS-REFERENCE TO RELATED APPLICATIONS

This is a U.S. National Stage Application under 35 U.S.C. 371 of International Application No. PCT/JP2017/046647 (not published in English), filed Dec. 26, 2017, which claims priority to Japanese Patent Application No. 2016-254282, filed Dec. 27, 2016. The disclosures of the above applications are incorporated herein by reference.

FIELD

The present invention relates to a bag-shaped structure, a cuff, and a blood pressure monitor.

BACKGROUND

For the measurement of blood pressure, a cuff is wrapped around an upper arm, a wrist, etc., and a bag-shaped structure included in this cuff is inflated. Then the internal pressure of the bag-shaped structure is decreased. Based on a change in pulse wave or Korotkoff sound caused in the process of decreasing the internal pressure, the highest blood pressure and the lowest blood pressure are determined.

In recent years, width reduction of this cuff has attracted attention.

Jpn. Pat. Appln. KOKAI Publication No. 2006-158876 discloses a cuff for a blood pressure monitor that is suitable for width reduction. This cuff for a blood pressure monitor comprises an air bag including a first bag member and a second bag member. When the cuff is fitted on a living body, the first bag member is positioned on the outer side in the thickness direction and the second bag member is positioned on the inner side in the thickness direction. The first bag member includes a first inflation/deflation space, and the second bag member includes a second inflation/deflation space. The second bag member is formed by laying a single-layer resin sheet on a living body side's outer surface of the first bag member, and welding the periphery of this sheet to the living body side's outer surface of the first bag member. The welded portion of the first bag member to which the resin sheet is welded is provided between two end portions arranged in the width direction of the first inflation/deflation space.

SUMMARY OF THE INVENTION

The flexibility of the bag-shaped structure also affects the artery occlusion characteristics. That is, a cuff including a bag-shaped structure formed of a highly flexible sheet conforms sufficiently to a living body when the bag-shaped structure is inflated. Thus, such a cuff is advantageous in terms of artery occlusion characteristics.

However, the inventors of the present invention have found that, in general, a bag-shaped structure formed of a sheet having an excellent flexibility tends to become loose when it is repeatedly inflated and deflated, that is, such a bag-shaped structure has a low creep resistance.

It is an object of the present invention to provide a bag-shaped structure excellent in both of creep resistance and flexibility.

According to a first aspect of the present invention, there is provided a bag-shaped structure including a layer made of a thermoplastic elastomer foam.

According to a second aspect of the present invention, there is provided a bag-shaped structure according to the first aspect, comprising one or more sheets including a first portion that applies a pressure to a living body, wherein the first portion includes the layer made of the foam.

According to a third aspect of the present invention, there is provided a bag-shaped structure according to the second aspect, wherein the one or more sheets further include a second portion that faces the first portion, and a third portion that connects an end of the first portion and an end of the second portion together, and the third portion comprises the layer made of the foam, and has an bellows structure that promotes deformation in a direction that the first portion and the second portion move away from each other when pressure in a space surrounded by the first to third portions is increased.

According to a fourth aspect of the present invention, there is provided a bag-shaped structure according to any one of the first to third aspects, wherein an expansion ratio of the foam is in a range of 1.5 to 8.

According to a fifth aspect of the present invention, there is provided a bag-shaped structure according to any one of the first to fourth aspects, wherein the foam has a closed-cell structure.

According to a sixth aspect of the present invention, there is provided a bag-shaped structure according to any one of the first to fifth aspects, wherein the thermoplastic elastomer has a Shore A hardness of 60 or more.

According to a seventh aspect of the present invention, there is provided a bag-shaped structure according to any one of the first to sixth aspects, wherein a thickness of the layer made of the foam is in a range of 0.10 mm to 0.50 mm.

According to an eighth aspect of the present invention, there is provided a bag-shaped structure according to any one of the first to seventh aspects, wherein the thermoplastic elastomer is thermoplastic polyurethane resin.

According to a ninth aspect of the present invention, there is provided a cuff for a blood pressure monitor, including the bag-shaped structure according to any one of the first to eighth aspects in a manner such that the layer made of the foam is positioned on a living body's side when the bag-shaped structure is fitted on the living body.

According to a tenth aspect of the present invention, there is provided a blood pressure monitor comprising the cuff according to the ninth aspect.

According to the first aspect, a layer made of a thermoplastic elastomer foam is used. Thus, both of a high creep resistance and an excellent flexibility can be attained.

According to the second aspect, the bag-shaped structure comprises one or more sheets including a first portion that applies a pressure to a living body, and the first portion includes the layer made of the foam. Thus, both of a high creep resistance and excellent artery occlusion characteristics can be attained.

According to the third aspect, one or more sheets further include a second portion that faces the first portion, and a third portion that connects an end of the first portion and an end of the second portion together. The third portion includes the layer made of the foam, and has a bellows structure that promotes deformation in a direction that the first portion and the second portion move away from each other when pressure in a space surrounded by the first to third portions is increased. Thus, a high creep resistance and more excellent artery occlusion characteristics can be attained.

According to the fourth aspect, an expansion ratio of the foam is in a range of 1.5 to 8. Thus, a performance that is particularly excellent in creep resistance and flexibility can be attained.

According to the fifth aspect, the foam has a closed-cell structure. This enables the bag-shaped structure to have a simplified structure, thereby achieving the reduction in manufacturing cost.

According to the sixth aspect, the thermoplastic elastomer has a Shore A hardness of 60 or more. Thus, a particularly excellent creep resistance can be achieved.

According to the seventh aspect, a thickness of the layer made of the foam is in a range of 0.10 mm to 0.50 mm. Thus, the risk of tearing, etc., is low. Furthermore, in the case of using the bag-shaped structure in a cuff, for example, particularly excellent artery occlusion characteristics can be attained. If the thickness of the foam-made layer is too small, the ratio of the thickness of a skin layer to the sheet thickness is increased. Thus, the physical properties of the skin layer stand out, so that the effect of foam may not appear remarkably. Here, the skin layer means a layer having a high density on the member surface, which is generated at the time of forming foamed plastics.

According to the eighth aspect, the thermoplastic elastomer is thermoplastic polyurethane resin. The thermoplastic polyurethane resin is a material that is particularly suitable for achieving both of a high creep resistance and an excellent flexibility when the thermoplastic polyurethane resin forms a foamed sheet.

According to the ninth aspect, the bag-shaped structure according to any one of the first to eighth aspects is used in a cuff for a blood pressure monitor, and the layer made of the foam is positioned on a living body's side when the cuff for the blood pressure monitor is fitted on the living body. Thus, both of a high creep resistance and excellent artery occlusion characteristics can be achieved.

According to the tenth aspect, a blood pressure monitor uses the cuff according to the ninth aspect. Thus, in addition to a high creep resistance, highly-accurate measurement of blood pressure values can be achieved.

DETAILED DESCRIPTION

Hereinafter, embodiments of the present invention will be described with reference to the drawings. Elements having same or similar functions are denoted by the same reference numerals, and redundant explanations will be omitted.

<Blood Pressure Monitor>

Figure 1:
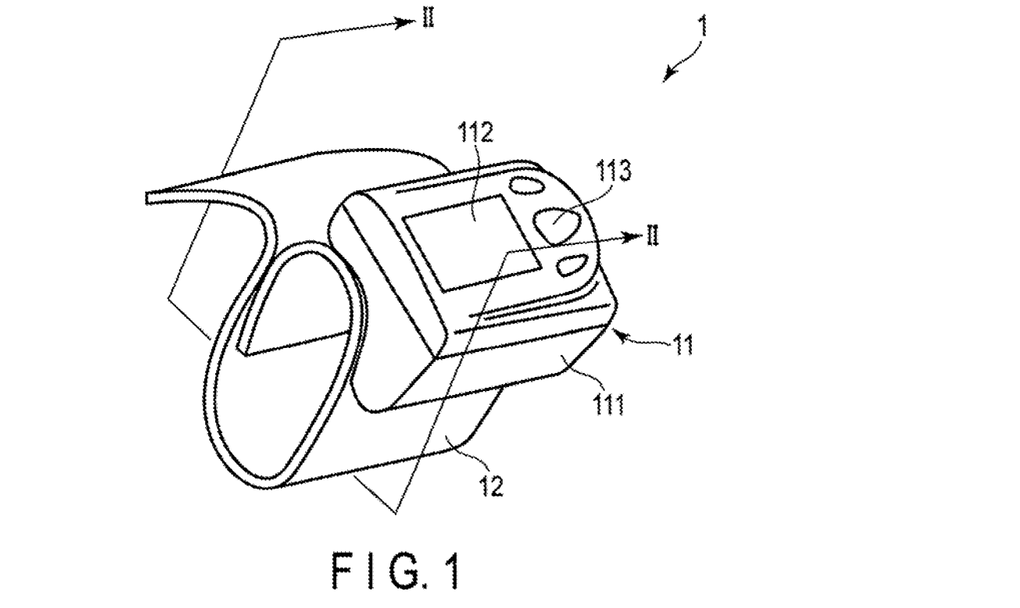
FIG. 1 is a perspective view schematically showing a blood pressure monitor according to one embodiment of the present invention.
Figure 2:
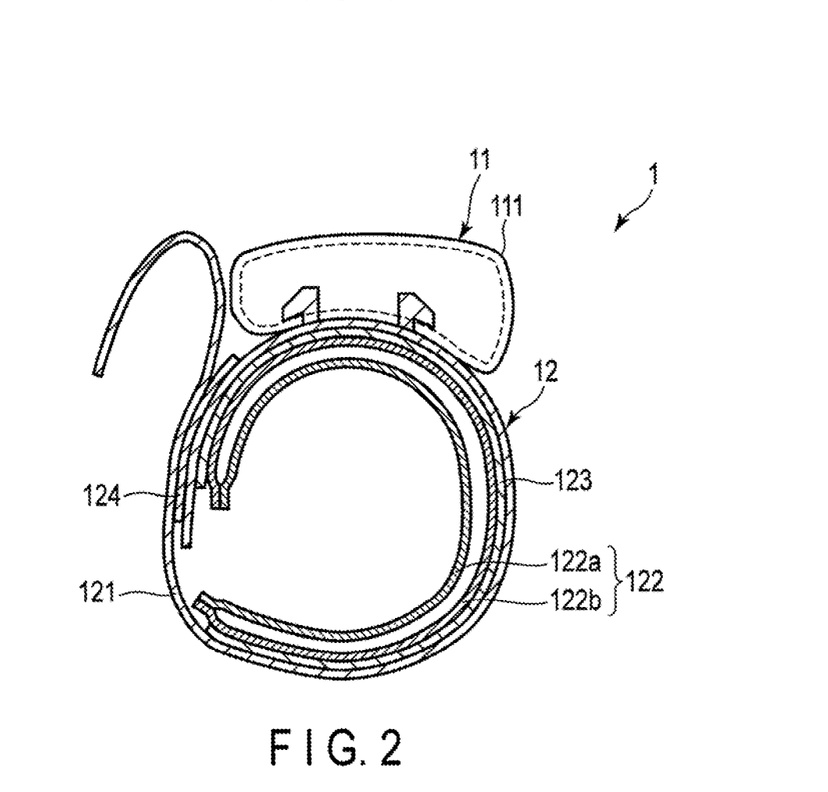
FIG. 2 is a cross-sectional view taken along line II-II of the blood pressure monitor in FIG. 1.

FIG. 1 is a perspective view schematically showing a blood pressure monitor according to one embodiment of the present invention. FIG. 2 is a cross-sectional view taken along line II-II of the blood pressure monitor in FIG. 1.

The blood pressure monitor 1 shown in FIG. 1 is an electronic wrist blood pressure monitor. The blood pressure monitor 1 includes an apparatus body 11 and a cuff 12.

The apparatus body 11 includes a housing 111, a display unit 112, and an operation unit 113. The apparatus body 11 further includes a flow path, a pump, a valve, a pressure sensor, a control unit, and a power supply unit (none of which are shown).

The upper part of the housing 111 includes openings for the display unit 112 and the operation unit 113. Furthermore, the lower part of the housing 111 is provided with a configuration for detachably fixing the apparatus body 11 to the cuff 12, in this case, recesses in which claws provided in the cuff 12 are inserted.

The display unit 112 is installed in the housing 111 so as to display images at the position of the opening provided in the upper part of the housing 111. The display unit 112 is, for example, a liquid crystal display or an organic electroluminescence display. The display unit 112 displays various types of information including a measurement result such as blood-pressure values of, e.g., the highest and lowest blood pressures, a heart rate, etc.

The operation unit 113 includes buttons for a user to, e.g., start/stop measurement, turn on/off the power supply, select functions, and make various settings. The operation unit 113 is installed in the housing 111 so that those buttons are exposed to the external space of the housing 111 at the position of the opening described above. The operation unit 113 outputs electric signals corresponding to commands or information input via the buttons.

According to an example, the flow path has a structure branched in four directions and includes four openings. One of those openings is connected to a supply/exhaust port of the bag-shaped structure 122 included in the cuff 12.

The pump is installed in the housing 111. An exhaust port of the pump is connected to another one of the openings included in the flow path. The pump is, for example, a rolling pump. The pump discharges compressed air from its exhaust port.

The valve is installed in the housing 111. The valve is connected to yet another one of the openings included in the flow path. The valve is a valve whose operation is controllable using electric power, for example, a solenoid valve. The valve opens and closes the opening to which the valve is attached.

The pressure sensor is installed in the housing 111. The pressure sensor is connected to the remaining one of the openings included in the flow path. The pressure sensor is, for example, a piezoresistive type pressure sensor. The pressure sensor detects pressure within the flow path and outputs an electric signal corresponding to this pressure.

The control unit is installed in the housing 111. The control unit is electrically connected to the display unit 112, the operation unit 113, the pump, the valve, and the pressure sensor, and supplies electric power to them. Furthermore, the control unit controls the operation of the display unit 112, the pump, and the valve based on electric signals output from the operation unit 113 and the pressure sensor. For example, when an electric signal corresponding to the start of measurement is supplied from the operation unit 113, the control unit controls the operation of the valve and the pump in a manner so that the valve is closed and then the pump starts driving. The control unit then determines a timing for stopping the operation of the pump, based on electric signals output from the pressure sensor, and controls the operation of the pump and the valve in a manner so that the pump stops operating at the determined timing and then the valve is gradually opened. Subsequently, the control unit obtains a measurement result such as blood-pressure values of the highest and lowest blood pressures, and a heart rate, from electric signals output from the pressure sensor, and outputs video signals corresponding to the measurement result to the display unit 112.

The power supply unit is installed in the housing 111. The power supply unit includes a battery. The power supply unit supplies electric power to the control unit.

The cuff 12 is detachably attached to the apparatus body 11. The cuff 12 is wrapped around a living body, specifically, a wrist of the living body and inflates in this state so as to press an artery.

As shown in FIG. 2, the cuff 12 includes a cover member 121, a bag-shaped structure 122, a curler 123, and a fastener 124.

The cover member 121 is installed in a manner to face a living body with the bag-shaped structure 122 interposed therebetween when the cuff 12 is fitted on the living body. The cover member 121 is a sheet having poor stretchability. The cover member 121 forms a structure having a bag shape extending in one direction. This direction corresponds to a direction in which the cuff 12 is wrapped around when the cuff 12 is fitted on a living body.

As will be described later, the cover member 121 supports the bag-shaped structure 122 and the curler 123, and enables the cuff 12 to be wrapped around a living body. Furthermore, when the bag-shaped structure 122 is inflated, the cover member 121 suppresses inflation toward the side opposite to a living body without hindering inflation toward the living body.

The bag-shaped structure 122 is supported by the cover member 121. As described above, the bag-shaped structure 122 includes the supply/exhaust port, and this supply/exhaust port is connected to one of the openings of the flow path included in the apparatus body 11. The bag-shaped structure 122 may include a supply port and an exhaust port instead of the supply/exhaust port.

When the pump is driven with the cuff 12 being fitted on a living body and the valve being closed, the bag-shaped structure 122 inflates and as a result, the cuff 12 occludes an artery of the living body. Subsequently, when the driving of the pump is stopped and the valve is opened, the bag-shaped structure 122 deflates and as a result, the pressure applied to the living body by the cuff 12 decreases, and the flow of blood is resumed. Details of the bag-shaped structure 122 will be described later.

The curler 123 is positioned between the cover member 121 and the bag-shaped structure 122. The curler 123 is fixed to the cover member 121 and the bag-shaped structure 122 by adhesion means such as a double-sided tape. The curler 123 is an elastic member made of, for example, resin such as polypropylene. Furthermore, the curler 123 has a shape curved in its longitudinal direction. This enables the curler 123 to bend the cuff 12 in its longitudinal direction, thereby facilitating the attachment of the cuff 12 to a living body. The curler 123 can be omitted.

The fastener 124 functions to fix one end of the cover member 121 to the other end when the cuff 12 is fitted on a living body. The fastener 124 is, for example, a hook-and-loop fastener. In this case, a hook surface of the hook-and-loop fastener is provided in one of regions that are paired with each other and are positioned on a surface of the cover member 121 in a manner to face each other when the cuff 12 is fitted on a living body, whereas a loop surface of the hook-and-loop fastener is provided in the other one of the regions.

<Bag-Shaped Structure>

Next, the bag-shaped structure 122 will be described in detail with reference to FIGS. 3 and 4.

Figure 3:
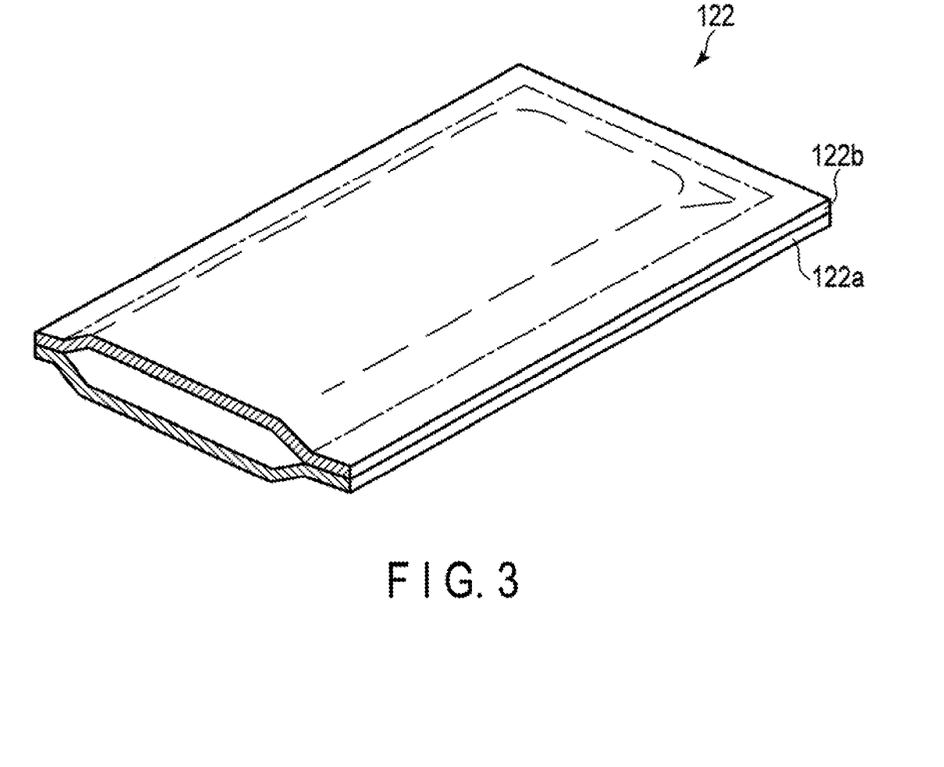
FIG. 3 is a broken perspective view of a bag-shaped structure included in the blood pressure monitor shown in FIGS. 1 and 2.

FIG. 3 is a broken perspective view of the bag-shaped structure included in the blood pressure monitor shown in FIGS. 1 and 2. FIG. 4 is a cross-sectional view of the bag-shaped structure included in the blood pressure monitor shown in FIGS. 1 and 2.

Figure 4:
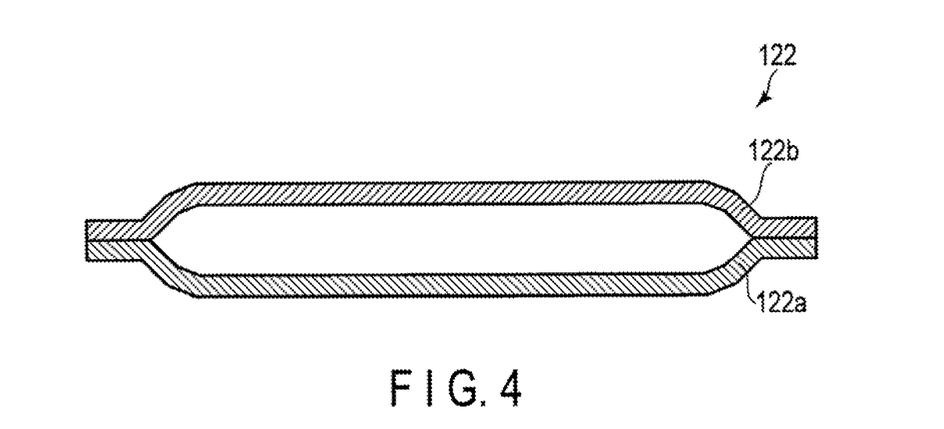
FIG. 4 is a cross-sectional view of the bag-shaped structure included in the blood pressure monitor shown in FIGS. 1 and 2.

The bag-shaped structure 122 shown in FIGS. 3 and 4 includes a layer made of a thermoplastic elastomer foam. In the sheets forming the bag-shaped structure 122, a first portion that is positioned between an internal space of the bag-shaped structure 122 and a living body when the cuff 12 is fitted on a living body includes this layer made of the thermoplastic elastomer foam.

The bag-shaped structure 122 shown in FIGS. 3 and 4 includes two sheets, sheets 122a and 122b. The sheets 122a and 122b are bonded to each other at their peripheral portions. This bonding can be performed by laser welding, high frequency welding, hot press welding, or adhesion with an adhesive or a double-sided tape.

The sheet 122a contains a thermoplastic elastomer foam. Furthermore, the sheet 122a has a single-layer structure, and the foam has a closed-cell structure. The closed-cell structure provides the sheets with flexibility, and a wall of resin with high hardness that is present in the vicinity of each bubble moderates the anisotropy of stress to thereby increase creep resistance. Thus, the closed-cell structure is advantageous especially in that flexibility and creep resistance, which are contrary physical properties, are satisfied at the same time.

As long as the sheet 122a includes the layer made of the thermoplastic elastomer foam, the sheet 122a may have a multilayer structure. The other layers in combination with the layer made of the thermoplastic elastomer foam are preferably made of an elastomer, and are more preferably made of a thermoplastic elastomer. As long as one or more of the other layers in combination with the layer made of the thermoplastic elastomer foam has a gas barrier property, the layer made of the thermoplastic elastomer foam may have an open-cell structure.

The sheet 122b is made of an elastomer, for example, a thermoplastic elastomer. The sheet 122b may include the layer made of the thermoplastic elastomer foam, or may not include this layer. In the former case, for example, the sheet 122b can adopt the structure exemplified for the sheet 122a. In the latter case, the sheet 122b may have a single-layer structure or a multilayer structure. As an example, herein, it is assumed that the sheet 122b is made of a non-foamed thermoplastic elastomer.

The thermoplastic elastomer foam can be formed by, for example, a melt foam molding method, a cast foam molding method, or a solid phase foam molding method.

As the thermoplastic elastomer, for example, polyurethane resin (TPU), vinyl chloride resin (PVC), ethylene-vinyl acetate resin (EVA), polystyrene resin (TPS), polyolefin resin (TPO), polyester resin (TPEE), and polyamide resin (TPA) can be used. As the thermoplastic elastomer, it is preferable to use thermoplastic polyurethane resin.

As the thermoplastic elastomer, for example, thermoplastic polyurethane resin having a Shore A hardness preferably in the range of 60 or higher, more preferably in the range of 70 to 95, is used. Here, the Shore A hardness is a durometer hardness obtained by a type A durometer hardness test specified in JIS K6253-3: 2012 ("Rubber, vulcanized or thermoplastic—Determination of hardness—Part 3: Durometer method"). In the case of using the thermoplastic elastomer having the Shore A hardness in the above range, the bag-shaped structure 122 that is particularly excellent in creep resistance can be obtained.

The Shore A hardness of the thermoplastic polyurethane resin can be adjusted, for example, by changing the type of compound to be used. Alternatively, the Shore A hardness of the thermoplastic polyurethane resin can be adjusted by changing the ratio of a soft segment content to a hard segment content.

The foam of the thermoplastic elastomer has an expansion ratio preferably in the range of 1.5 to 8, and more preferably in the range of 2 to 6. With the foam having the expansion ratio in the above range, the bag-shaped structure 122 can achieve an excellent performance particularly in the conformability of the cuff 12 to a living body when the bag-shaped structure 122 is inflated, and creep resistance. Here, the expansion ratio indicates a ratio of the volume of foamed plastic to a volume of a solid having the same mass, that is, a value obtained by dividing an apparent density of the foamed plastic by a density of synthetic resin before foaming. For example, when foam obtained by foaming a thermoplastic elastomer of 1.3 $g/m^3$ has the apparent density of 0.65 $g/m^3$, this foam has the expansion ratio of 2. The density of the thermoplastic elastomer before foaming is equal to the density of the thermoplastic elastomer obtained by melting the foam, removing bubbles therefrom, and then curing it.

For a sheet that is brought in direct contact with a skin, the thermoplastic elastomer blended with an additive such as silica, calcium carbonate, or talc may be used. Usage of such an additive improves the sheet in terms of skin sensation. The amount of this additive is preferably 10 parts by mass or less, and more preferably in the range from 0.5 parts by mass to 2.0 parts by mass, with respect to 100 parts by mass of thermoplastic elastomer.

Regarding the thickness of the layer made of the thermoplastic elastomer foam or the thickness of the sheet forming the bag-shaped structure 122 in the corresponding position, which is the thickness of the sheet 122a according to the example shown in FIGS. 3 and 4, is preferably in the range from 0.10 mm to 0.50 mm, and more preferably in the range from 0.15 mm to 0.30 mm. If this thickness is too small, the risk of tearing, for example, may be incurred. If this thickness is too large, there is a possibility that the conformability of the cuff 12 to a living body at the time of inflation of the bag-shaped structure 122 is not sufficient to attain excellent artery occlusion characteristics.

<Measurement of Blood Pressure Value>

Next, the measurement of blood pressure values using the blood pressure monitor 1 will be described with reference to FIGS. 1, 2, 5, and 6.

Figure 5:
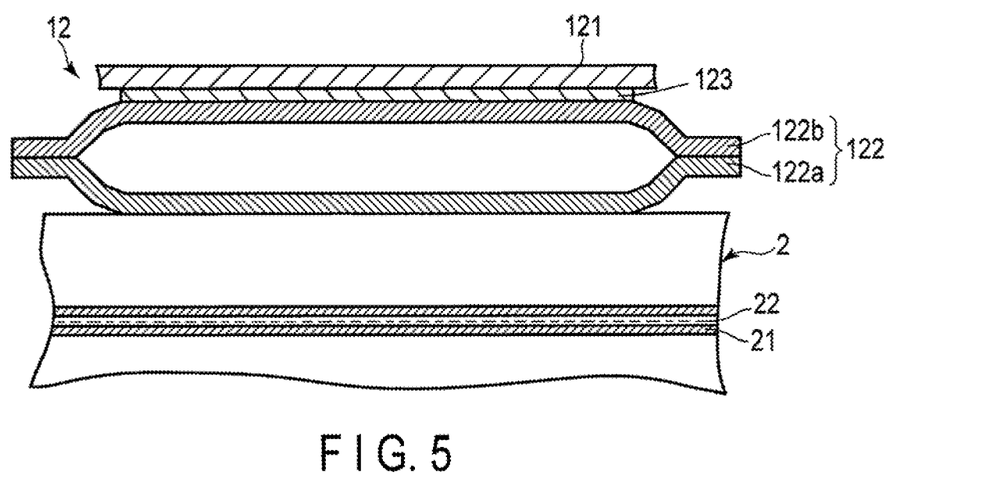
FIG. 5 is a cross-sectional view schematically showing a state in which a cuff included in the blood pressure monitor shown in FIGS. 1 and 2 is fitted on a living body.
Figure 6:
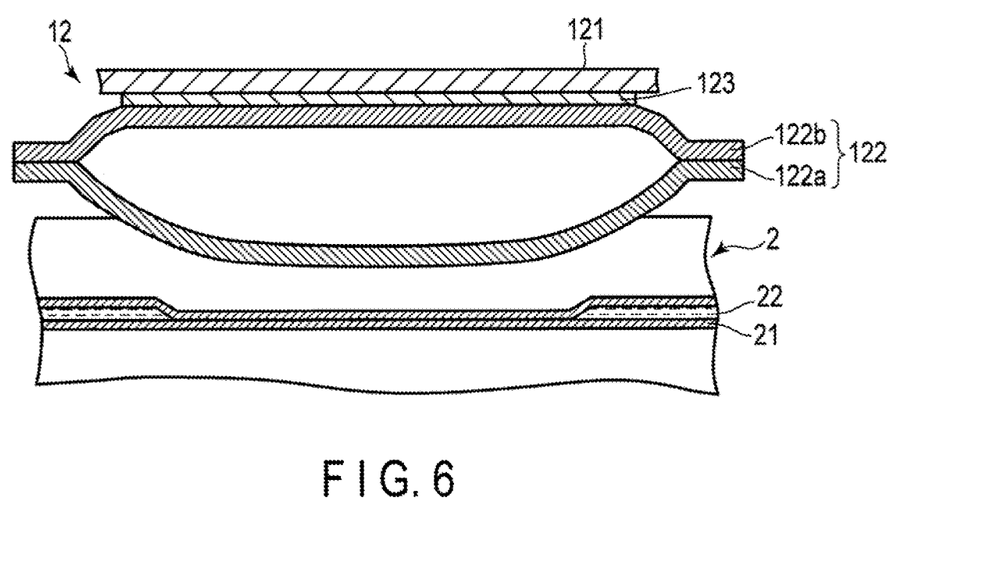
FIG. 6 is a cross-sectional view schematically showing the same state as in FIG. 5 except that the bag-shaped structure included in the cuff is inflated.

FIG. 5 is a cross-sectional view schematically showing a state in which the cuff included in the blood pressure monitor shown in FIGS. 1 and 2 is fitted on a living body. FIG. 6 is a cross-sectional view showing the same state as in FIG. 5 except that the bag-shaped structure included in the cuff shown in FIG. 5 is inflated. In the following description, a person to be measured performs all operations by himself or herself.

To measure a blood pressure value, a person to be measured first places the cuff 12 on the wrist 2 as shown in FIG. 5. Next, the person to be measured operates the operation unit 113 shown in FIG. 1 to input a command corresponding to the start of measurement of a blood pressure value.

When this command is input, the operation unit 113 outputs an electric signal corresponding to the start of measurement to the control unit. The control unit supplied with this signal controls the operation of the valve and the pump in a manner so that the valve is closed and the pump starts driving. In this manner, the bag-shaped structure 122 starts inflating.

The pressure sensor detects a pressure in the internal space of the bag-shaped structure 122 and outputs an electric signal corresponding to this pressure to the control unit. Based on this electric signal, the control unit determines whether or not the pressure in the internal space of the bag-shaped structure 122 has reached a predetermined level for blood pressure measurement. The control unit then controls the operation of the pump so that the pump halts driving when this pressure has reached the aforementioned level. Immediately after the pump halts driving, as shown in FIG. 6, the bag-shaped structure 122 is sufficiently inflated, and the cuff 12 occludes an artery 21 at the position of a wrist 2.

Thereafter, the control unit controls the operation of the valve so that the valve is gradually opened. When the valve is opened, the air inside the bag-shaped structure 122 is exhausted, thereby lowering the pressure in the internal space. In this decompression process, the flow of blood 22 in the artery 21 is resumed. From electric signals output from the pressure sensor in this process, the control unit obtains a measurement result such as blood-pressure values of, e.g., the highest and lowest blood pressures, a heart rate, etc., and outputs video signals corresponding to the measurement result to the display unit 112 shown in FIG. 1.

When the aforementioned video signals are supplied, the display unit 112 displays on its screen the measurement result such as blood-pressure values of, e.g., the highest and lowest blood pressures, a heart rate, etc. In this way, the measurement is terminated.

<Effect>

The aforementioned bag-shaped structure 122 includes the layer made of the thermoplastic elastomer foam. With such a layer, its cell structure provides the sheets with flexibility, and at the same time, a wall of resin with high hardness that is present in the vicinity of each bubble moderates the anisotropy of stress to thereby increase creep resistance. In other words, a high creep resistance and an excellent flexibility can be simultaneously achieved. That is, while using a thermoplastic elastomer with which a high creep resistance is achievable, an excellent flexibility can also be realized by foaming the thermoplastic elastomer into foam. Also, adopting the foam in this way enables the reduction in material costs and weight.

<Modifications of Bag-Shaped Structure>

The bag-shaped structure 122 described above can be modified in various ways.

Figure 7:
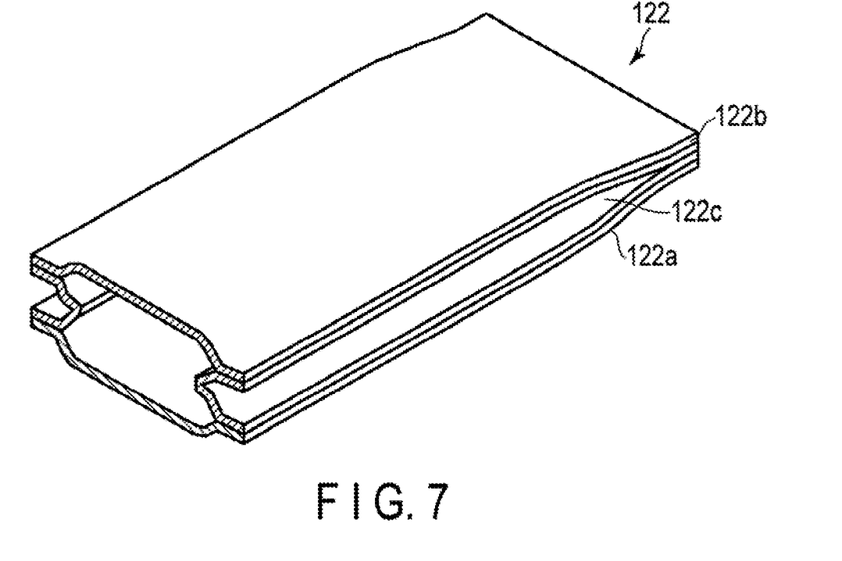
FIG. 7 is a broken perspective view schematically showing a first modification of the bag-shaped structure shown in FIGS. 3 and 4.
Figure 8:
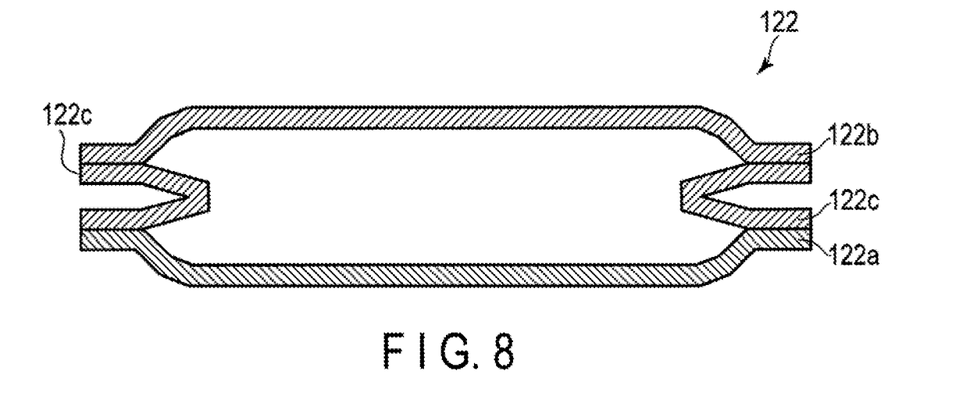
FIG. 8 is a cross-sectional view of the bag-shaped structure according to the first modification.
Figure 9:
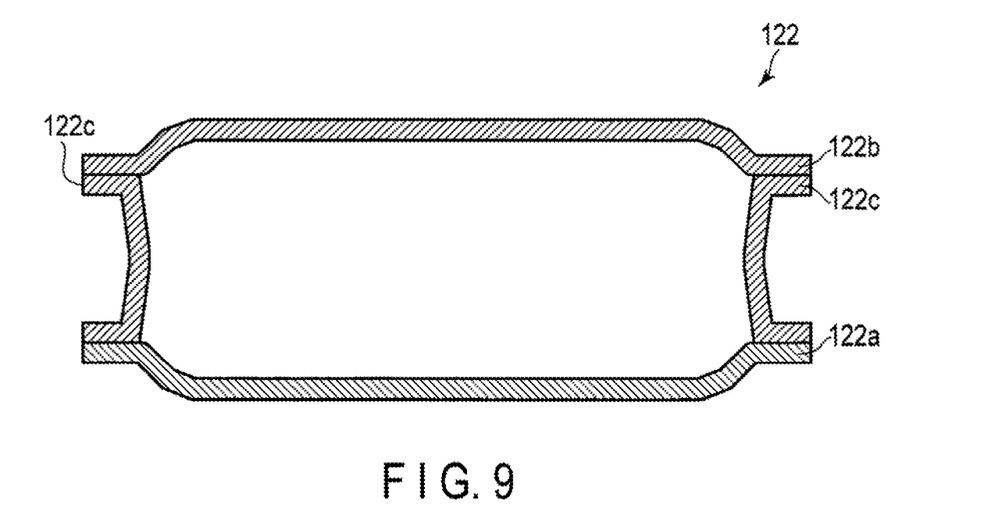
FIG. 9 is a cross-sectional view schematically showing a state in which the bag-shaped structure according to the first modification is inflated.

FIG. 7 is a broken perspective view schematically showing a first modification of the bag-shaped structure shown in FIGS. 3 and 4. FIG. 8 is a cross-sectional view of the bag-shaped structure according to the first modification. FIG. 9 is a cross-sectional view schematically showing a state in which the bag-shaped structure according to the first modification is inflated.

The sheets forming the bag-shaped structure 122 shown in FIGS. 7 and 8 include a first portion, a second portion, and a third portion. The first portion is positioned between an internal space of the bag-shaped structure 122 and a living body when the cuff 12 is fitted on the living body. The second portion faces the first portion with the internal space of the bag-shaped structure 122 interposed therebetween when the cuff 12 is fitted on the living body, on a wrist 2 herein. The third portion connects an end of the first portion and an end of the second portion together. The third portion has a bellows structure that promotes deformation of the bag-shaped structure 122 in a direction that the first portion and the second portion move away from each other when the pressure in the internal space of the bag-shaped structure 122 is increased. Herein, the first portion corresponds to the sheet 122a. The second portion corresponds to the sheet 122b. The third portion corresponds to a pair of sheets 122c.

The sheets 122c are disposed between the sheets 122a and 122b, on the sides of the internal space of the bag-shaped structure 122, respectively. Each of the sheets 122c has a shape that extends in the longitudinal direction of the bag-shaped structure 122 and has two ends extending in this longitudinal direction, in which one end is bonded to one end of the sheet 122a that extends in its longitudinal direction, and the other end is bonded to one end of the sheet 122b that extends in its longitudinal direction.

Each of the sheets 122c has a shape that is curved or bent in a manner so that its center portion extending in the longitudinal direction of the bag-shaped structure 122 projects toward the internal space of the bag-shaped structure 122. Each of the sheets 122c is, for example, a molded article formed so as to be curved or bent at its center portion. Each of the sheets 122c may be a composite body formed by stacking two sheet pieces and bonding them together along one side.

The sheets 122c are made of a non-foamed elastomer, for example, a non-foamed thermoplastic elastomer. The elastomer forming the sheets 122c may be the same as or different from the elastomer forming the sheet 122b. In the former case, the structure including the sheets 122c and the sheet 122b may be a molded article formed integrally.

The sheets 122a to 122c are bonded together in a manner described above, thereby forming a tubular structure. In this structure, both openings are sealed, whereby the bag-shaped structure 122 is formed. In this bag-shaped structure 122, a supply/exhaust port, or a supply port and an exhaust port are provided at any position.

The bag-shaped structure 122 shown in FIGS. 7 and 8 is easily deformable into a more flattened structure, for example, by pressing the bag-shaped structure 122 in its thickness direction. Furthermore, when compressed air is supplied to the internal space of the bag-shaped structure 122, the sheets 122c are easily deformable from a curved or bent state to a spread state as shown in FIG. 9. Accordingly, when compressed air is supplied to the internal space of the bag-shaped structure 122, the bag-shaped structure 122 can be greatly increased in thickness. The inflation in the width direction of the bag-shaped structure 122 can be caused only after the inflation in the thickness direction is completed, for example. In addition, since the sheets 122c are made of a non-foamed elastomer, their flexibility can be reduced more easily than the sheet 122a made of a thermoplastic elastomer foam. Therefore, in the case of using the cuff 12 including the bag-shaped structure 122, more excellent artery occlusion characteristics can be attained by causing the inflation in the thickness direction of the bag-shaped structure 122 while suppressing the inflation in the width direction thereof.

Figure 10:
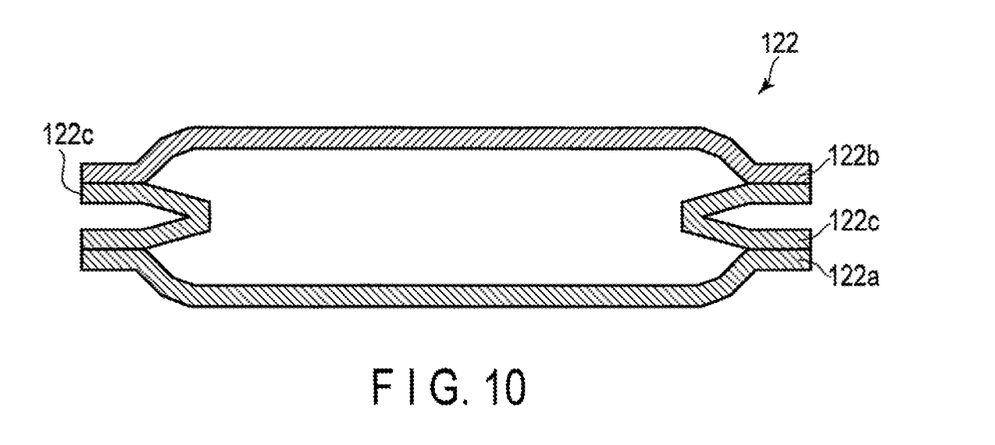
FIG. 10 is a cross-sectional view of a bag-shaped structure according to a second modification.

FIG. 10 is a cross-sectional view of a bag-shaped structure according to a second modification.

This bag-shaped structure 122 has a structure similar to that of the bag-shaped structure 122 described with reference to FIGS. 7 to 9 except that the sheets 122c include the layer made of the thermoplastic elastomer foam. These sheets 122c of the bag-shaped structure 122 can adopt the above-described configuration of the sheet 122a. The sheets 122c and the sheet 122a may be the same in a layer composition, a thickness, and a material, or may be different in one or more of such. In the former case, the structure including the sheets 122c and the sheet 122a may be a molded article formed integrally.

In the bag-shaped structure 122 shown in FIG. 10, the sheets 122c can be made flexible more easily than those in the bag-shaped structure 122 described with reference to FIGS. 7 to 9, without sacrificing creep resistance. As compared to the bag-shaped structure 122 having the sheets 122c with a lower flexibility, the bag-shaped structure 122 having the sheets 122c with a higher flexibility is deformable into a state in which the sheets 122c are spread as shown in FIG. 9, at an earlier stage in the process of increasing the pressure in the internal space.

In this manner, the inflation characteristic of the bag-shaped structure 122 can be adjusted according to the structure and material adopted for the sheets 122c.

<Other Blood Pressure Monitors>

In the above, the blood pressure monitor 1 shown in FIGS. 1 and 2 was described as an application example of the bag-shaped structure 122. However, the bag-shaped structure 122 can also be used in other blood pressure monitors.

Figure 11:
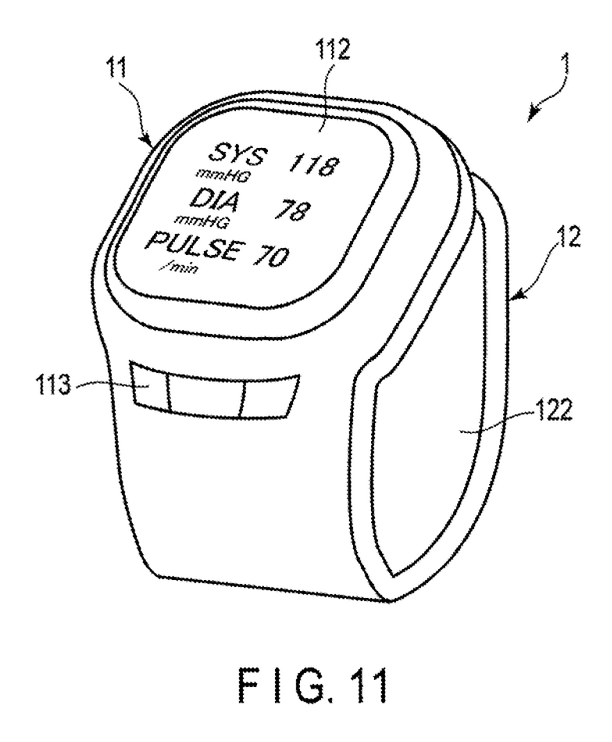
FIG. 11 is a perspective view schematically showing a blood pressure monitor according to another embodiment of the present invention.

FIG. 11 is a perspective view schematically showing a blood pressure monitor according to another embodiment of the present invention.

The blood pressure monitor 1 shown in FIG. 11 is an electronic wrist blood pressure monitor of a wristwatch type. This blood pressure monitor 1 is smaller than the blood pressure monitor 1 described with reference to FIGS. 1 and 2. In this type of the blood pressure monitor 1, the apparatus body 11 and the cuff 12 are integrally formed. Other than these, the blood pressure monitor 1 shown in FIG. 11 has substantially the same structure as that of the blood pressure monitor 1 described with reference to FIGS. 1 and 2.

With the bag-shaped structure 122, in the case where the width of the cuff 12 is reduced to, for example, 40 mm or less, or even 20 mm or less, both of excellent creep resistance and flexibility can be achieved.

The blood pressure monitor having the bag-shaped structure 122 included in the cuff is not necessarily a blood pressure monitor for a wrist. For example, the blood pressure monitor having the bag-shaped structure 122 included in the cuff may be a blood pressure monitor for an upper arm.

The blood pressure monitor having the aforementioned bag-shaped structure 122 included in the cuff may supply air to the bag-shaped structure 122 via a manual pump. Furthermore, instead of determining a blood pressure value based on a change in pulse wave detected by the pressure sensor, the blood pressure monitor having the aforementioned bag-shaped structure 122 included in the cuff may determine a blood pressure value based on a change in Korotkoff sound detected by a microphone or a stethoscope. In addition, instead of using the pressure sensor, the blood pressure monitor having the aforementioned bag-shaped structure 122 included in the cuff may use a mercury pressure gauge.

EXAMPLES

Specific examples of the present invention are described below.

Manufacture of Bag-Shaped Structure

Example 1

The bag-shaped structure 122 described with reference to FIGS. 3 and 4 was manufactured. In this example, the sheets 122a and 122b used the same thermoplastic elastomer. As this thermoplastic elastomer, thermoplastic polyurethane resin (TPU) having a Shore A hardness of 95 was used. The sheet 122a was manufactured by a melt foam molding. The expansion ratio for this was 1.5. Further, the thickness of the sheet 122a was 0.15 mm.

Example 2

The bag-shaped structure was manufactured by the same method as in Example 1 except that the expansion ratio was set to 2.

Example 3

The bag-shaped structure was manufactured by the same method as in Example 1 except that the expansion ratio was set to 3.

Example 4

The bag-shaped structure was manufactured by the same method as in Example 1 except that the expansion ratio was set to 6.

Example 5

The bag-shaped structure was manufactured by the same method as in Example 1 except that that the expansion ratio was set to 8.

Example 6

The bag-shaped structure was manufactured by the same method as in Example 1 except that thermoplastic polyurethane resin having a Shore A hardness of 60 was used.

Example 7

The bag-shaped structure was manufactured by the same method as in Example 6 except that the expansion ratio was set to 2.

Example 8

The bag-shaped structure was manufactured by the same method as in Example 6 except that the expansion ratio was set to 3.

Example 9

The bag-shaped structure was manufactured by the same method as in Example 6 except that the expansion ratio was set to 6.

Example 10

The bag-shaped structure was manufactured by the same method as in Example 6 except that the expansion ratio was set to 8.

Comparative Example 1

The bag-shaped structure was manufactured by the same method as in Example 1 except that the sheet 122a was a non-foamed sheet.

Comparative Example 2

The bag-shaped structure was manufactured by the same method as in Example 6 except that the sheet 122a was a non-foamed sheet.

<Evaluation>

With respect to the bag-shaped structures obtained by the methods described above, artery occlusion characteristics and creep resistance were evaluated.

(Evaluation of Artery Occlusion Characteristics)

By using each of the aforementioned bag-shaped structures in a cuff of a wrist blood pressure monitor, blood pressure values were measured. Then, the variation, that is, the measurement accuracy was examined. Specifically, blood pressure values were measured by alternately using a commercially available upper-arm blood pressure monitor (Model HEM-7120 manufactured by Omron Healthcare Co., Ltd.) and a wrist blood pressure monitor manufactured in each Example or Comparative Example. A blood pressure value was measured 10 times in total for each of the blood pressure monitors. Thereafter, the standard deviation was calculated with respect to differences between blood pressure values obtained by the upper-arm blood pressure monitor and blood pressures obtained by the wrist blood pressure monitor manufactured in each Example or Comparative Example. The bag-shaped structure which exhibited the standard deviation of 7 mmHg or more was evaluated as "x", whereas the bag-shaped structure which exhibited the standard deviation of less than 7 mmHg was evaluated as "o".

(Evaluation of Creep Resistance)

The inflation and deflation were alternately repeated for each of the aforementioned bag-shaped structures to examine the looseness of the sheet 122a. Specifically, three bag-shaped structures were prepared for each of Examples 1 to 4 and Comparative Example 1, and a cycle of inflation and deflation with a pressure fluctuation of 300 mmHg was repeated 10,000 times for each bag-shaped structure. Thereafter, the ratio of the difference between the dimension of the sheet 122a after 10,000 cycles and the dimension of the initial sheet 122a to the dimension of the initial sheet 122a was calculated with respect to the three bag-shaped structures. The arithmetic mean of these ratios was regarded as looseness. The bag-shaped structure which exhibited a looseness value of 5% or more was evaluated as "x", whereas the bag-shaped structure which exhibited a looseness value of less than 5% was evaluated as "o".

Evaluation results of artery occlusion characteristics and creep resistance are shown in Table 1 and Table 2.

TABLE 1

|  | Example 1 | Example 2 | Example 3 | Example 4 | Example 5 | Example 6 |
| --- | --- | --- | --- | --- | --- | --- |
| Sheet structure | Low expansion | Low expansion | Medium expansion | High expansion | High expansion | Low expansion |
| Expansion ratio | 1.5 | 2 | 3 | 6 | 8 | 1.5 |
| Shore A hardness | 95 | 95 | 95 | 95 | 95 | 60 |
| Artery occlusion characteristics (Standard deviation of blood pressure value) | ○ (6 mmHg) | ○ (5 mmHg) | ○ (3 mmHg) | ○ (3 mmHg) | ○ (3 mmHg) | ○ (4 mmHg) |
| Creep resistance (Looseness) | ○ (3%) | ○ (3%) | ○ (2%) | ○ (3%) | ○ (4%) | ○ (4%) |

TABLE 2

|  | Example 7 | Example 8 | Example 9 | Example 10 | Comparative Example 1 | Comparative example 2 |
| --- | --- | --- | --- | --- | --- | --- |
| Sheet structure | Low expansion | Medium expansion | High expansion | High expansion | Non-expansion | Non-expansion |
| Expansion ratio | 2 | 3 | 6 | 8 | — | — |
| Shore A hardness | 60 | 60 | 60 | 60 | 95 | 60 |
| Artery occlusion characteristics (Standard deviation of blood pressure value) | ○ (3 mmHg) | ○ (3 mmHg) | ○ (3 mmHg) | ○ (3 mmHg) | x (10 mmHg) | ○ (5 mmHg) |
| Creep resistance (Looseness) | ○ (3%) | ○ (2%) | ○ (3%) | ○ (4%) | ○ (4%) | x (6%) |

As shown in Tables 1 and 2, in the case of using the bag-shaped structures according to Examples 1 to 10, not only an excellent creep resistance but also highly-accurate measurement were achieved. In the case of using the bag-shaped structures according to Examples 3 to 5 and 7 to 10, the measurement of blood pressure values was realized with particularly small standard deviations. On the other hand, in the case of using the bag-shaped structures according to Comparative Example 1, excellent creep resistance was achieved; however, the measurement accuracy was such that the values varied widely. In addition, in the case of using the bag-shaped structures according to Comparative Example 2, highly-accurate measurement was realized; however, the creep resistance was low.

The invention claimed is:

1. A cuff for a blood pressure monitor comprising:
a bag-shaped structure comprising one or more sheets including a first portion that is configured to contact and apply a pressure to a living body,
wherein the first portion includes a gas barrier layer and a layer made of a thermoplastic elastomer foam having an open-cell structure, the thermoplastic elastomer foam is a foam of thermoplastic polyurethane resin, and the thermoplastic polyurethane resin has a Shore A hardness of 60 or more.

2. The cuff for the blood pressure monitor according to claim 1, wherein the one or more sheets further include a second portion that faces the first portion, and a third portion that connects an end of the first portion and an end of the second portion together, and wherein the third portion comprises a layer made of the thermoplastic elastomer foam, and has a bellows structure that promotes deformation in a direction that the first portion and the second portion move away from each other when pressure in a space surrounded by the first to third portions is increased.

3. The cuff for the blood pressure monitor according to claim 1, wherein a thickness of the layer made of thermoplastic elastomer foam is in a range of 0.10 mm to 0.50 mm.

4. The cuff for the blood pressure monitor according to claim 1 wherein the layer made of the thermoplastic elastomer foam is configured to be positioned on a living body's side when the bag-shaped structure is fitted on the living body.

* * * * *